(12) United States Patent
Buck et al.

(10) Patent No.: US 7,731,835 B2
(45) Date of Patent: *Jun. 8, 2010

(54) ELECTROCHEMICAL SENSOR AND METHOD FOR CONTINUOUS ANALYTE MONITORING

(75) Inventors: Harvey B. Buck, Indianapolis, IN (US); Matthias Essenpreis, Fremont, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1044 days.

This patent is subject to a terminal disclaimer.

(21) Appl. No.: 11/038,970

(22) Filed: Jan. 19, 2005

(65) Prior Publication Data

US 2005/0211572 A1    Sep. 29, 2005

Related U.S. Application Data

(63) Continuation of application No. 10/069,308, filed as application No. PCT/US00/25631 on Sep. 19, 2000, now Pat. No. 7,045,054.

(60) Provisional application No. 60/154,731, filed on Sep. 20, 1999.

(51) Int. Cl.
*G01N 27/327* (2006.01)

(52) U.S. Cl. ............... 205/792; 205/777.5; 204/403.14; 204/403.04

(58) Field of Classification Search ................ 204/403.01–403.15; 205/777.5, 778, 792
See application file for complete search history.

(56) References Cited

U.S. PATENT DOCUMENTS

| | | | |
|---|---|---|---|
| 4,224,125 A | 9/1980 | Nakamura et al. | |
| 4,225,410 A | 9/1980 | Pace | |
| 4,376,689 A | 3/1983 | Nakamura et al. | |
| 4,999,632 A | 3/1991 | Parks | |
| 5,120,420 A | 6/1992 | Nankai et al. | |
| 5,134,057 A * | 7/1992 | Kuypers et al. ............. | 430/325 |

(Continued)

FOREIGN PATENT DOCUMENTS

EP    0396788 A1    11/1990

(Continued)

OTHER PUBLICATIONS

Derwent English language abstract of Hitachi JP 62-133937, patent published on Jun. 17, 1987.*

(Continued)

*Primary Examiner*—Alex Noguerola
(74) *Attorney, Agent, or Firm*—Bose McKinney & Evans LLP (57) ABSTRACT

Sensors and a method for detecting an analyte are described. Sensors each have a volume of a hydrophilic medium that retains an amount of analyte proportionate to the concentration of analyte in a biological fluid, electrodes and a redox enzyme in contact with medium, and an electron transfer mediator. The fluid contacts sensors and at initially predetermined intervals intermittently applies a potential to electrode sufficient to oxidize the mediator and sensing current through electrode as a function of the duration of the applied potential. The applied mediator oxidizing applied potential is maintained for a period of time sufficient to determine the rate of change of current with time through electrode. The current flow is correlated with the current flow for known concentrations of the analyte in medium.

27 Claims, 4 Drawing Sheets

U.S. PATENT DOCUMENTS

| | | | |
|---|---|---|---|
| 5,141,868 A | 8/1992 | Shanks et al. |
| 5,192,415 A | 3/1993 | Yoshioka et al. |
| 5,232,574 A | 8/1993 | Saika et al. |
| 5,243,516 A | 9/1993 | White |
| 5,262,035 A | 11/1993 | Gregg et al. |
| 5,264,103 A | 11/1993 | Yoshioka et al. |
| 5,264,104 A | 11/1993 | Gregg et al. |
| 5,264,105 A | 11/1993 | Gregg et al. |
| 5,288,636 A | 2/1994 | Pollmann et al. |
| 5,352,351 A | 10/1994 | White et al. |
| 5,366,609 A | 11/1994 | White et al. |
| 5,405,511 A | 4/1995 | White et al. |
| 5,413,690 A | 5/1995 | Kost et al. |
| 5,437,999 A | 8/1995 | Diebold et al. |
| 5,438,271 A | 8/1995 | White et al. |
| 5,494,831 A | 2/1996 | Kindler |
| 5,575,895 A | 11/1996 | Ikeda et al. |
| 5,589,326 A | 12/1996 | Deng et al. |
| 5,593,852 A | 1/1997 | Heller et al. |
| 5,735,273 A | 4/1998 | Kurnik et al. |
| 5,741,284 A | 4/1998 | Karlsson |
| 5,786,439 A | 7/1998 | Van Antwerp et al. |
| 5,820,551 A | 10/1998 | Hill et al. |
| 5,906,921 A | 5/1999 | Ikeda et al. |
| 6,096,825 A | 8/2000 | Garnier |
| 6,312,888 B1 | 11/2001 | Wong et al. |

FOREIGN PATENT DOCUMENTS

| | | | |
|---|---|---|---|
| GB | 1 318 815 | | 5/1973 |
| JP | 62-133937 A | * | 6/1987 |
| JP | 64-012257 | | 1/1989 |
| JP | 09-033533 | | 2/1997 |
| WO | WO 91-09302 | | 6/1991 |
| WO | WO 93-06237 | | 4/1993 |
| WO | WO 96-06947 | | 3/1996 |
| WO | WO 98-35225 | | 8/1998 |
| WO | WO 98-58250 | | 12/1998 |

OTHER PUBLICATIONS

Hill, "The exploitation of the electrochemistry of proteins", Biochemical Society Transactions, vol. 11 (453-455).

Csoregi et al., "Design and Optimization of a Selective Subcutaneously Implantable Glucose Electrode Based on Wired Glucose Oxidase", Anal. Chem. 1995, 67. 1240-1244.

Koryta, "Electroanalytical Methods Used in Medicine and Biology", Medical and Biological Applications of Electrochemical Devices, 1980, A Wiley-Interscience Publication, 7-11.

Liu et al. "Fabrication of Miniature $PO_2$ and pH Sensors Using Microelectronic Techniques", Diabetes Care 5: 275-277, May-Jun. 1982.

Turner et al., "Applications of electron transfer between biological systems and electrodes", Biochemical Society Transactions 11.445-448 (1983).

Updike et al., "The Enzyme Electrode", Nature, vol. 214, 986-988, Jun. 3, 1967.

Wang et al. "Improved Ruggedness for Membrane-Based Amperometric Sensors Using a Pulsed Amperometric Method", Anal. Chem. 1997, 69, 4482-4489.

Yang et al. "Development of a Dual Glucose-Oxygen Sensor System for Continuous In Vivo Monitoring", Journal of Clinical Engineering, vol. 22, No. 1, Jan.-Feb. 1997 (55-63).

Gough et al. "Development of the Implantable Glucose Sensor What are the Prospects and Why is it Taking so Long", Prospectives in Diabetes, D93-511, Apr. 7, 1995 (14pp).

CAPLUS abstract of Tang et al. ("Oxygen effects on glucose measurements with glucose dehydrogenase- and oxidase-based test strips for point-of-care testing," Critical Care Medicine (2001), 29(5), 1062-1070).

Adelou et al. ("Pulsed-amperometric detection of urea in blood samples on a conducting polypyrrole-urease biosensor," analytica Chimica Acta 341 (1997) 155-160).

* cited by examiner

ELECTROCHEMICAL SENSOR AND METHOD FOR CONTINUOUS ANALYTE MONITORING

CROSS-REFERENCE TO RELATED APPLICATIONS

This application is a continuation of U.S. application Ser. No. 10/069,308 filed Feb. 20, 2002, now U.S. Pat. No. 7,045,054 which claims priority to PCT/US00/25631 filed Sep. 19, 2000, which claims priority to U.S. Provisional Application No. 60/154,731 filed Sep. 20, 1999.

FIELD OF THE INVENTION

This invention relates to sensors for detecting the presence or quantity of an analyte in a biological fluid. More particularly, this invention is directed to a sensor adapted particularly for indwelling or implanted use. Analyte concentrations are measured electrochemically in a contained detection retention volume of an analyte-permeable medium separated from the biological fluid with a semi-permeable membrane.

BACKGROUND AND SUMMARY OF THE INVENTION

There has been a significant research and development effort directed to the development of electrochemical sensors capable of detecting the presence and/or quantity of biologically significant analytes. Many, if not most of such analyte sensing devices are in the form of a test strip comprising a test fluid containment space pretreated with an analyte-dependent detection composition and electrodes for contact with test fluid delivered into the test fluid containment space. Electrical conductors extend from the electrodes to an area on the test strip for connection to a hand held or table mounted preprogrammed sensor reading device. Typically a biological fluid is delivered to the sample fluid containment area or volume and the sensor reading device is programmed to apply a predetermined potential to the electrodes after a predetermined period of time following delivery of the fluid sample to the sample containment space. Current flow is then measured responsive to said applied potential to provide an indication of the presence and/or concentration of the target analyte.

Some of such electrochemical sensors are constructed to prevent direct contact of the sample fluid with the electrodes by covering the electrodes with a semipermeable membrane or gel matrix material, which is insoluble in the test medium and permeable at least to the analyte of interest when in contact with said test medium.

There is a continuing need for the development of commercially feasible, multi-/continuous-use sensors for biologically significant analytes. In particular, there is need for development of biological sensors capable of being implanted or injected into a patient for periods ranging from several hours up to several weeks, months, or years and designed to provide accurate results without removal or recalibration to compensate for changes in diffusional properties of membrane components or for losses of enzyme activity and/or electron mediator elements. Such sensors would find application as components of artificial organs, for example an artificial pancreas, requiring continuous and/or regular monitoring of patient glucose levels. Such devices could also find use as reusable sensors for measuring analyte concentrations in bodily fluids in vitro, such as the analytical situations encountered by commercial labs performing analysis on patient fluid samples.

There are unique problems presented by the design and construction of biological sensors capable of repeated use in vitro and/or continuous use in vivo. Indeed, inherent in such functional requirements is the condition that the functional chemical component of the sensor be confined, i.e. not released from the sensor into the sample fluid during repeated and/or continuous use. The retention of the "active" chemical/electrochemical components of the biosensor can be accomplished by one of several techniques, alone or in combination. Thus the active components can be immobilized, for example, by covalent bonding to non-leachable components of the biosensor or by confining the biologically/electrically active components in a testing zone or volume by means of a membrane permeable at least by the analyte, but not by the contained, optionally covalently bound, enzymes, coenzymes, and/or electron mediators.

The implantable and/or reusable biosensors in accordance with the present invention are designed to retain the active sensor-dependent chemical components, typically in a hydrophilic matrix in an analyte retention volume. The active electrochemical species that cooperate in the sensor responsive to an applied potential to provide a current flow signal proportionate to the concentration of analyte diffused into the retention volume can optionally be covalently bound to non-leachable components of the retention volume including, but not limited to, an electrode of an electrode system, a wall of the enclosure portion of the sensor for defining, at least in part, the retention volume, to microspheres or other microparticulate solids contained in the retention volume, to the retention volume contacting the side of a membrane, or to polymer components of the retention volume matrix. Alternatively the enzyme(s), the enzyme cofactor(s) and the electron mediator (s) can be selected to have a molecular weight sufficiently high to preclude any substantial diffusion of such components from the retention volume into the biological fluid being analyzed.

In one aspect of this invention the retention volume medium, alternatively denominated the "depletion volume medium" is in contact with the electrode system comprising an electrode capable of receiving electrons from or delivering electrons to the enzyme(s) via the electron mediator(s). Conductor elements extend from the electrode to a point on the device for allowing electrical communication of the electrode with a programmable controller. The controller can be programmed to apply a predetermined potential sequence to the electrode system including variable potential including either a mediator oxidizing potential or mediator reducing potential, variable pulse width and variable pulse intervals. The controller is also capable of sensing current flow responsive to applied potential(s) to the electrode system and comparing such data with control data previously obtained for said system to calculate and report analyte concentrations in the biological sample being analyzed and, optionally, to use such data to sense the performance status of the device and use such for modifying the then existing potential sequence protocol to optimize device function. Thus, for example, the sensor control can be modified periodically to adjust for differences in analyte diffusion efficiency across the membrane and/or changes in concentration of the active electron mediator and/or enzyme component(s) of the device without use of classical recalibration techniques.

In one embodiment of the invention the retention volume is defined or enclosed, at least in part, by an analyte-permeable membrane and the ratio of the retention volume to the surface area of the semipermeable membrane defining that volume, at least in part, is less than 2 mm, more preferably less than 1 mm. The low volume to surface area ratios are preferred in that they improve the rate of diffusional equilibrium between the fluid being tested and the retention volume medium, and thereby it works to minimize the refractory period (the recovery period) of the sensor.

In one preferred embodiment the enzyme component is selected so that it is substantially not capable of transferring electrons to or from any endogenous substance other than said analyte. Under such conditions the enzyme reaction responsible for providing a signal of analyte concentration cannot take place without a predetermined threshold potential being applied to the electrode system. The sensor can therefore be turned off to stop enzyme activity, optionally following a pulse of reducing potential to "deactivate" the mediator, and allow predictable concentration-gradient-based diffusion to work to rapidly "reset" the analyte concentration in the analyte detection/retention volume for the next programmed pulsed potential detection sequence.

In another embodiment of the present invention there is provided a method for monitoring analyte concentration using the sensor of this invention by contacting the sensor with the biological fluid being analyzed. Initially at predetermined intervals a potential is applied intermittently to the electrode system sufficient to oxidize the electron mediator in the retention volume, and the current flow through the electrode is sensed as a function of the duration of the applied potential. The applied mediator oxidizing potential is maintained at least for a period of time sufficient to determine the rate of change of current through the electrode as a function of duration of the applied potential. Values for the sensed current are correlated with values of current flow for known concentrations of the analyte. Alternatively the sensing protocol can comprise adjusting the potential to establish a predetermined current flow and thereafter sensing the rate of change of potential required to maintain said current flow for a predetermined time period.

In another embodiment the analyte concentration in a biological sample is measured as a function of the time dependent concentration of analyte in the retention volume following analyte depleting potential pulses. The rate of recovery concentration in the retention/depletion volume can be readily correlated with analyte concentration in the biological fluid contacting the sensor. The "diffusion status" of the membrane can be checked by a preprogrammed sequence from time-to-time during sensor use and numerical values associated with the sensed status can be used as input to modify the preprogrammed pulse sequence algorithms for subsequent sensor operation.

These and other features of the invention are described hereinbelow with reference to the drawings and the best mode known for carrying out the invention.

DETAILED DESCRIPTION OF THE INVENTION

The electrochemical sensor of this invention is designed to provide signals indicative of analyte concentration in a biological fluid. The sensor comprises an electrode in contact with a low volume of a hydrophilic medium for retaining an amount of analyte proportionate to the concentration of analyte in a biological fluid in contact with the sensor. The medium is selected to allow facile analyte diffusion through said medium alone or upon hydration of said medium prior to or consequent to sensor use. The sensor comprises an enclosure for the volume of hydrophilic medium. The enclosure is formed to expose the hydrophilic medium to the biological fluid so that analyte in the biological fluid diffuses into the hydrophilic medium until the concentration of analyte in the medium is equivalent to the concentration of analyte in the biological fluid. The rate of analyte mass diffusion into the retention volume is dependent on the analyte concentration gradient. The concentration of analyte in the retention/depletion volume may be measured electrochemically by cooperation of an electron mediator and a redox enzyme specific for the analyte, each forming part of or being in contact with the hydrophilic medium.

The hydrophilic medium can have a water concentration level less than, equal to or greater than the water content of the biological fluid. Thus the components of the hydrophilic medium including the enzyme and electron mediator components and a hydrophilic polymer can be used in construction of the sensor in a substantially dehydrated state, ready for rehydration prior to use or upon contact of the sensor with a biological fluid. It is important for sensor function that the analyte of interest is readily diffusible through the hydrophilic medium to enable a substantially homogeneous concentration of the analyte in the analyte retention volume, and a concentration that closely corresponds to analyte concentration in the biological fluid in contact with the sensor.

The sensor is constructed to have an enclosure or compartment for holding the analyte retention volume of the hydrophilic medium. The enclosure compartment is formed to expose the hydrophilic medium to the biological fluid when the sensor is in use. In one embodiment, the enclosure compartment is defined at least in part by a wall comprising an area of an analyte permeable membrane having a first side in contact with the hydrophilic medium and an opposite side for contact with the biological fluid when the sensor is in use. The analyte of interest, water, and other membrane permeable components of the biological fluid diffuses through the membrane and into the retention volume of hydrophilic medium until the concentration of analyte in the medium is proportionate to the concentration of analyte in the biological fluid contacting the analyte permeable membrane component of the sensor. It is appreciated that while a sensor in accordance with the present invention may include an analyte permeable membrane, such a membrane is not necessary to the operation of the sensor and as such is not required.

The sensor is constructed to provide an electrode in electrical contact with the hydrophilic medium. The electrode is typically formed of a conductive element such as carbon, silver, gold, platinum, palladium and the like and typically extends into or forms part of the walls of the container or chamber for the analyte retention volume of hydrophilic medium. In one embodiment the electrode is formed of platinum and the retention volume is defined as the space overlying the electrode. In another embodiment, the electrode can be formed of a graphite powder and the retention volume is defined by the intraparticulate spaces and, in at least one embodiment, an overlying analyte permeable membrane. In another embodiment the electrode is a component of an electrode system comprising a reference electrode and optionally an auxiliary electrode, which may be different or identical to the reference electrode. The electrode system can also comprise conductor elements for providing electrical communication between the electrode components of the system and a programmable controller to control the electrical potentials in said electrode system and to sense current flow through at least one of said electrodes responsive to said electrical potentials. Typically the programmable controller is constructed as a separate unit with electrical connectors adapted particularly for electrical communication between the controller and the electrode system of the sensor. The controller is typically a hand-held or table mounted unit capable of being reversibly connected to one or more biosensors and having data storage and data display elements.

The sensor for electrochemical analysis in accordance with this invention further comprises a redox enzyme and an electron mediator in contact with the hydrophilic medium. The enzyme is selected for its capacity to oxidize or reduce the analyte of interest. The enzyme is preferably selected as well for its lack of capacity for transferring electrons to or from substances other than said analyte that are capable of diffusing from the biological fluid into the analyte retention volume. Non-limiting examples of suitable enzymes include pyrroloquinoline quinone (PQQ)-dependent glucose dehydrogenase (GDH) (EC 1.1.99.17) or Hydroxybutyrate dehydrogenase (HBDH) (EC 1.1.1.30). Dehydrogenase enzymes for other diffusible analytes are known in the art and can be substituted dependent on the analyte of interest.

The electron mediator can be selected from any of a wide variety of electron mediators capable of facilitating transfer of electrons between the redox enzyme and a sensor electrode in contact with the medium containing or in contact with said enzyme and said mediator. A non-limiting example of a suitable mediator includes osmium (bis-bipyridyl) pyridinium chloride. It is appreciated, however, that a number of commercially available mediators, non-limiting examples of which are described in U.S. Pat. No. 5,589,326, the disclosure of which is expressly incorporated herein by reference, may be used in accordance with the present invention. The enzyme and electron mediator can be entrapped in a polymer matrix on the electrode. Optionally, the enzyme and electron mediator can be selected to minimize their diffusion through an analyte permeable membrane during sensor use or can be covalently bound to the walls of the enclosure or to hydrophilic polymer components of the retention medium to minimize, if not prevent, their diffusion from the retention medium volume through the membrane and into the biological fluid during sensor use.

Any of a wide variety of hydrophilic polymers, typically having a molecular weight in excess of 5000 Daltons and having polyanionic, polycationic, or polyhydric functionality can be used as a carrier or carrier matrix forming part of the hydrophilic medium component of the sensor. Examples of such polymers include cellulosic polymers such as cellulose acetate, hydroxy ethyl cellulose, polyethylene glycols, synthetic or natural gums such as guar or xanthan gums, alginic acid, poly (meth) acrylic acids and copolymers of acrylic acids and acrylic esters, glycosaminoglycans, and the like which polymers can be used. Additionally, electrically polymerized matrices from monomers such as pyrrole-3-acetic acid and pyrrole-3-carboxylic acid can serve as the hydrophilic matrix and/or enzyme entrapping matrix.

Such hydrophilic polymers can be used alone or in combination to provide a hydrated or hydratable matrix through which the targeted analyte is readily diffusible. Further, such polyfunctional hydrophilic polymers can be used to "anchor" or otherwise impair the diffusion of the enzyme or electron mediator components of the medium to minimize loss of such components from the retention volume during sensor use.

Thus, art-recognized electron mediators having, for example hydroxy, carboxy or amino functionality for example ferrocene carboxylic acid, can be coupled using art-recognized ester-forming or amide-forming coupling methodologies to form the hydrophilic medium for use in preparation of the present sensors. Additional mediator compounds that can be tethered to a polymeric matrix include redox reversible imidazole-osmium complexes. Non-limiting examples of such complexes include osmium-bipyridyl conjugates such as tris(bipyridyl) osmium complex characterized by fast mediation kinetics and low redox potential (+150 mV vs. Ag/AgCl). Another group of osmium complex labeled, electrochemically detectable conjugates include bis(bipyridyl) imidazolyl haloosmium complexes, which, like the tris(bipyridyl) osmium complexes are characterized by fast mediation kinetics and low redox potential (+150 mV vs. Ag/AgCl). The tris(bipyridyl) complexes have a redox potential sufficiently different from bis(pyridyl)imidazolyl chloroosmium complexes. The redox enzyme and an electron mediator can thus be inherently non-diffusible or chemically coupled with the high molecular weight components of the medium to render the enzyme and electron mediator components substantially not capable of diffusing through the analyte permeable membrane during sensor use in contact with a biological fluid.

The enzyme component of the sensor is typically of sufficient molecular weight that diffusional loss of that component through the semipermeable membrane is marginal over the typical period of sensor use. Such enzymes can be incorporated into the hydrophilic medium during device construction, as, for example, an enzyme lyophilizate formed by freeze drying a solution of enzyme in the presence of a hydrophilic monomer, for example, maltose or trehalose, or other enzyme stabilizing hydrophilic composition. The lyophilized enzyme can be retained in said medium during sensor manufacture and storage in a dehydrated state until rehydration prior to or during initial use of said sensor, thereby providing longer sensor shelf life.

Electron mediator components of the sensors of the present invention are not critical except for the fact that they should be selected or modified, for example by covalent bonding of polymer components of the hydrophilic matrix or the hydrophilic medium, to prevent or minimize diffusional loss of the electron mediator component from the analyte retention volume medium during the course of sensor use. The prior art is replete with reference to a wide variety of compounds including metal chelates and other metal complexes such as ferrocene, and more particularly carboxy ferrocene that can be readily coupled covalently to non-diffusible components of the hydrophilic medium.

The membrane components of the sensor constructs of this invention can be any biocompatible analyte permeable membrane, including for example cellulose acetate, polyurethane, and polycarbonate. Other polymeric biocompatible membranes suitable for use in biosensor construction are also well known in the art and any of such art-recognized analyte permeable membrane/membrane materials may be used in manufacture of the present sensors. Example of analyte permeable membranes, and as well electron mediators and redox enzymes are describe in U.S. Pat. No. 5,264,105, the specification of which is expressly incorporated herein by reference.

In one embodiment of the invention the hydrophilic matrix is bound on the surface of at least one of the electrodes of the electrode system. The hydrophilic matrix comprises an electron mediator covalently bound to a non-diffusible or poorly diffusible hydrophilic polymer component of the matrix. The redox enzyme is bound to a polymer component of the hydrophilic matrix as well. A sensor of the present invention, preferably already includes the electron mediator and redox enzyme components, which are exposed to analyte present in the retention volume of the sensor. Initially at predetermined intervals a potential is applied intermittently to the electrode system sufficient to oxidize the electron mediator and the current flow through the electrode is sensed as a function of the duration of the applied potential. The applied mediator oxidizing potential is maintained at least for a period of time sufficient to determine the rate of change of current through the electrode as a function of duration of the applied potential. Values for the sensed current are correlated with values of current flow for known concentrations of analyte.

In another embodiment of the invention the hydrophilic medium comprises either a polymeric electron mediator or an electron mediator covalently bound to a non-diffusible or poorly diffusible hydrophilic polymer component of the medium. The redox enzyme is included as a stabilized lyophilizate or is covalently bound itself to a polymer component of the hydrophilic medium. The hydrophilic medium also comprises polyfunctional components that can be reacted with difunctional crosslinking agents contacted with the surface of said hydrophilic medium to form in situ an analyte permeable membrane on the surface of the hydrophilic medium. Thus for example a polyhydric polymer or a di- or trihydric, preferably high molecular weight, monomer component of the hydrophilic medium can be reacted, for example, with a polyisocyanate, for example a diisocyanate in the vapor phase, to form a polymer skin or membrane on the surface of the hydrophilic medium. The permeability of the membrane can be controlled by the length of exposure of the polyhydric medium surface to the multifunctional crosslinker. Thus, for example, 1,4-benzene diisocyanate can be vaporized in a chamber. Sensor constructs comprising the hydrophilic medium, preferably already including the electron mediator and redox enzyme components, having an exposed surface is introduced into the chamber for a period of time sufficient to form a biocompatible membrane on the surface of the hydrophilic medium to define in conjunction with other sensor components for example, a simple planar non-conductive substrate, the enclosure for the analyte retention volume component of the sensor.

Figure 1:
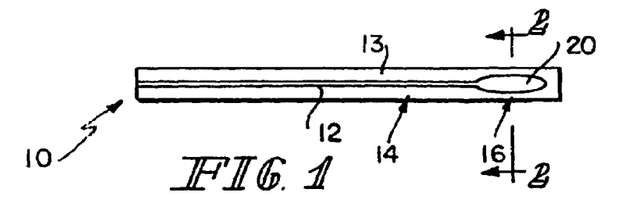
FIG. 1 is a plan view of a sensor in accordance with the present invention.

With reference to FIG. 1, there is provided in one embodiment of this invention a sensor 10 utilizing a thin-film gold electrode 12 on an inert substrate 14. In cross section (see FIG. 2) a sensing portion 16 includes gold electrode 12 on a surface 13 of inert substrate 14, spacer layers 18 and a diffusion-limiting membrane 20 having small or no pores. Membrane 20 can be formed as a separate sheet and applied to spacer layers 18 resting on gold electrode 12 and inert substrate 14 to complete definition of an enclosure for a depletion volume 22 filled with a hydrophilic medium 24. The enzyme and mediator may be immobilized, for example by entrapment in a hydrophilic matrix on the gold electrode 12. Additionally, it is contemplated that the enzyme and mediator may be immobilized by covalent bonding to a wall 26 of enclosure 22 or to overlying membrane 20 or such components can be freely diffusing and selected to have minimal membrane permeability. Diffusion-limiting membrane 20 can be selected from art-recognized analyte permeable membranes and adhered to a surface 28 of spacer layer 18 to complete enclosure 22 for the analyte retention/depletion volume. Alternatively the analyte permeable membrane can be formed in situ by cross-linking polyfunctional hydrophilic polymer and/or monomer components of the enzyme/mediator reagent layer. Still further, sensor 10 may be formed without membrane 20. It is understood that as used throughout the disclosure, that like reference numerals are used to denote like components.

Figure 3:
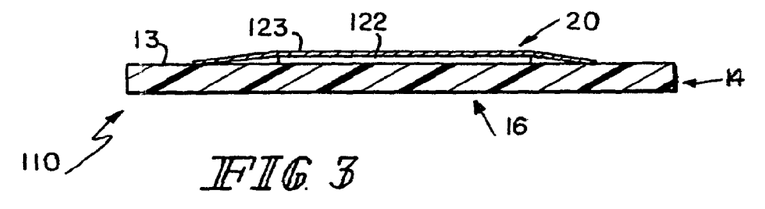
FIG. 3 illustrates a cross-sectional view similar to FIG. 2 but the electrode is of different construction.

With reference to FIG. 3, sensor 110 is provided in accordance with this invention. Sensor 110 includes an electrode formed of a porous/particulate carbon layer wherein the depletion volume is defined by the interstitial spaces between carbon/graphite particles (not shown). Thus a carbon-enzyme-mediator reagent layer 122 can be formed, for example by screen printing, a carbon/graphite suspension comprising a redox enzyme, and a nondiffusible or poorly diffusible, for example a polymeric, electron mediator in combination with one or more optionally non-electron mediating, polyfunctional polymers. The suspension is typically deposited on a conductor element (not shown) on an inert substrate. The diffusion-limiting analyte permeable membrane 20 can be applied, similar to that mentioned above, as a preformed polymer sheet applied and sealed over a surface 123 of the carbon electrode or membrane 20 can be formed by coating the exposed printed electrode having an intraparticulate polyfunctional polymer matrix with a polymer in solution. See, for example, International Patent Application No. WO 98/17995 for non-limiting examples of polymer membranes for coating biosensors.

Figure 4:
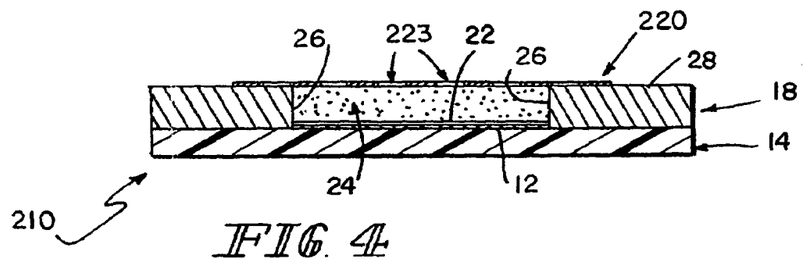
FIG. 4 is similar to FIG. 2 illustrating a cross-sectional view of a sensor in accordance with this invention having a diffusion-limiting membrane with large pores.

With reference to FIG. 4, which is similar to FIG. 1, sensor 210 of the present invention includes a diffusion-limiting membrane 220 that is formed to have large pores 223 for enhanced glucose diffusion. The mediator and enzyme components are preferably immobilized by entrapment in a hydrophilic matrix on electrode 12, by covalent bonding to nondiffusible polymeric components of hydrophilic medium 24, or to surfaces 26 of sensor enclosure 22 for the retention volume.

Figure 5:
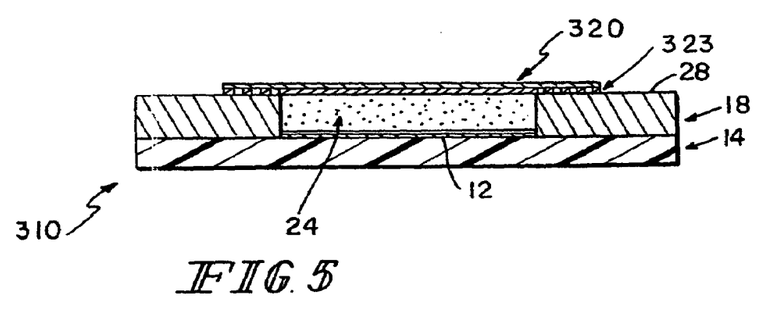
FIG. 5 is similar to FIG. 4 illustrating a cross-sectional view of a sensor embodiment of this invention wherein diffusion into the retention volume is via pores on the periphery of an otherwise non-permeable membrane component.

With reference to FIG. 5, there is provided another embodiment in the invention. Sensor 310 is similar to that illustrated in FIGS. 1 and 4 with the exception that membrane 320 overlying hydrophilic medium 24 is nonpermeable itself. Membrane 320 is provided with peripheral porosity allowing diffusion of glucose or other analytes into the retention/depletion volume.

The biochemical sensor of this invention can be constructed in any form adapted for the intended use. Thus, sensors intended for repeated laboratory use can be constructed in the form of an elongated probe having the sensor element itself located at one end and electrical conductors connecting the electrode component of the sensing element to points of electrical attachment of the probe sensor to a programmable sensor controller. Alternatively the present electrochemical sensor can be constructed using art recognized micro scale manufacturing techniques to produce needle-like sensors capable of being implanted or injected into a site for indwelling sensor applications.

The electrochemical sensor of this invention can be utilized for monitoring analyte concentrations in biological fluids. The method comprises the steps of contacting the biological fluid with the sensor and at initially predetermined intervals intermittently applying a potential to the electrode sufficient to oxidize the electron mediator. The current passing through the electrode is then sensed as a function of the duration of the applied potential. The applied mediator-oxidizing potential is maintained for at least a period of time sufficient to determine the rate of change of current with time through said electrode. The sensed current flow is then correlated with current flow for known concentrations of said analyte in the retention/detection medium. Alternatively the sensor can be constructed to comprise at least a working electrode and a reference electrode and optionally an auxiliary electrode, which may be identical with the referenced electrode. At initially predetermined intervals a potential is applied sufficient to establish a predetermined level of current flow between the working electrode and the auxiliary electrode. And the potential difference between the working and reference electrodes necessary to establish said level of current flow is measured and maintained for a period of time sufficient to determine the rate of change of potential necessary to maintain said current flow through said electrode. The potential measurements are then correlated with potential measurements recorded for known concentrations of analyte in the biological fluid.

The applied potentials, the duration of the potential pulses, and the intervals between potential pulses are entered into a programmable controller used in conjunction with the sensor for analyte measurements. In one embodiment of the invention the intervals between the intermittent applied potentials are less than the time necessary for the concentration of the analyte in the retention volume to equilibrate with that in the biological fluid in contact with the analyte permeable membrane. In another embodiment the intervals are increased incrementally for a series of applied potentials, and the concentration of the analyte and the biological fluid is determined as a function of the rate of increase in analyte concentration in the retention volume. The intervals between applied potential pulses can be modified based on previous measurements to adjust for variations in sensor performance deriving from loss or degradation of redox enzyme and electron mediator components and/or change in diffusion characteristics of either the analyte permeable membrane or the retention volume medium. Alternatively the duration of the applied potential pulse is modified based on previous measurements of sensed sensor performance status. In still another embodiment of sensor operation the intervals between measurements is substantially equal to or greater than the time required for the analyte concentration in the retention volume to equilibrate with that in the biological fluid.

FIGS. 6-9 present graphic illustrations of sample measurement algorithms wherein the potential of the electrode is controlled over a period of time to vary between a potential at which no oxidation of mediator occurs ($E_0$) to a mediator oxidizing potential (E1) and a potential at which reduction of the mediator takes place (E−1). The potential protocol to be applied in any given situation depends on sensor status, the form of the sensor, and the nature of the electron mediator and redox enzyme. The protocol for sensor operation can be optimized by empirical measurement and observations by the skilled user.

Figure 6:
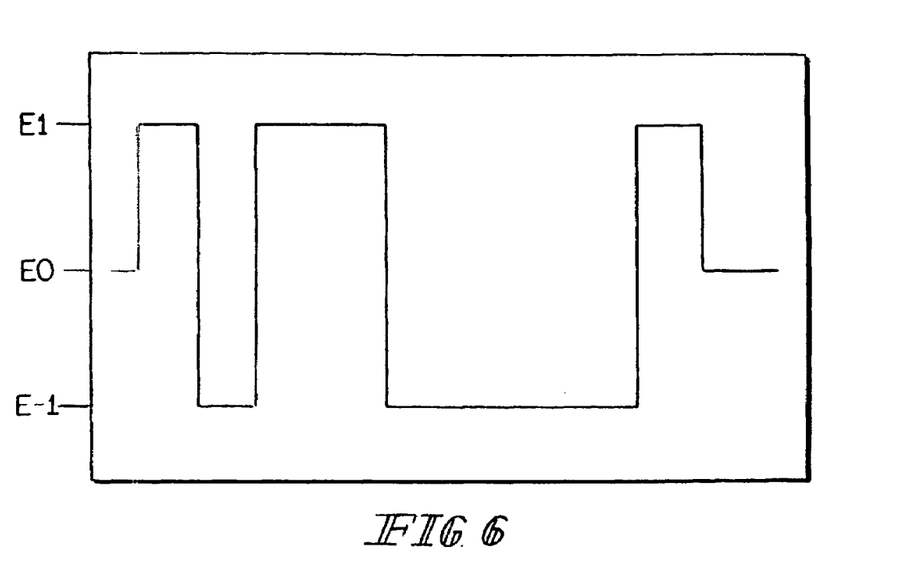
FIG. 6 is a graphic representation of a pulse sequence in which two pulses of oxidative potential of different duration are applied to the sensor, interspersed with recovery intervals with reducing potential.

Specifically, FIG. 6 shows a pulse sequence in which two pulses of oxidative potential of different duration are applied to the sensor, interspersed with recovery intervals with reducing potential. By comparing the current profile from the first pulse with that from the second, information on the rate of enzymatic turnover of the substrate, and the rate of electron diffusion within the sensor may be obtained. Between the oxidative potential applications, the reducing potential ensures that all of the mediator is returned to it's initial state prior to the application of the next oxidizing potential.

Figure 7:
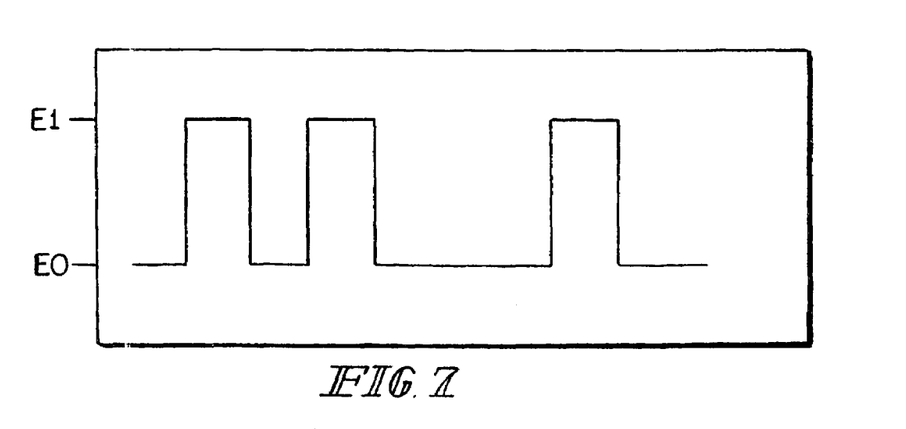
FIG. 7 is a graphic representation of a pulse sequence in which the duration of the intervals between the pulses is changed.

FIG. 7 shows a sequence in which the duration of the intervals between the pulses is changed. By comparing the current observed from the second pulse to that from the first, information on the recovery time of the sensor can be gained. The recovery time yields information not only on analyte concentration, but also on diffusion into the hydrophilic matrix. Measuring the rest potential of the sensor between the potentiostatic pulses also provides information on the sensor recovery.

Figure 8:
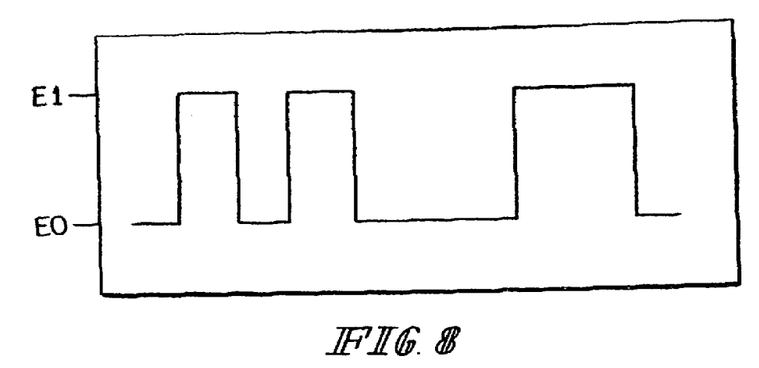
FIGS. 8-9 are graphic representations of measurement protocols, which combine changes in the pulse interval with changes in the pulse width.
Figure 9:
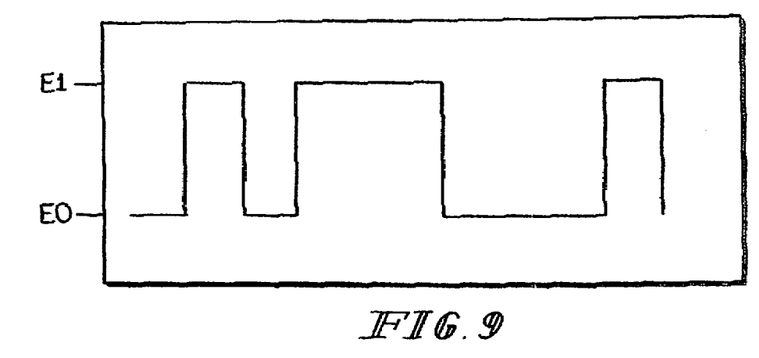

FIGS. 8-9 demonstrate measurement protocols, which combine changes in the pulse interval with changes in the pulse width. The controller can select from a variety of sequences and durations of amperometric measurement intervals and recovery intervals to determine not only the analyte concentration, but also probe the condition of the sensor for enzyme activity, diffusion of substrate and mediator within the sensor, and diffusion of substrate into the sensor.

The nature and construction of the controller used with the present electrochemical sensor is not critical provided that the controller can be programmed to apply the appropriate potential pulse profiles to the sensor electrode or electrode system and to sense the current flow as a function of potential in time. A separate sensor status assessment protocol can be implemented in which the controller implements a protocol that allows computation of diffusion characteristics of the depletion volume and membrane from current data. The controller can be programmed to adjust measurement intervals and pulse widths based on computed diffusion times and determined substrate concentration. Both chronoamperometry and chronocolometry may be used to determine sensor status and substrate concentration. Ideally the controller should also be capable of applying a reducing potential to the electrode to reduce the mediator and thereby decrease consumption of analyte between measurements.

Example 1

Figure 2:
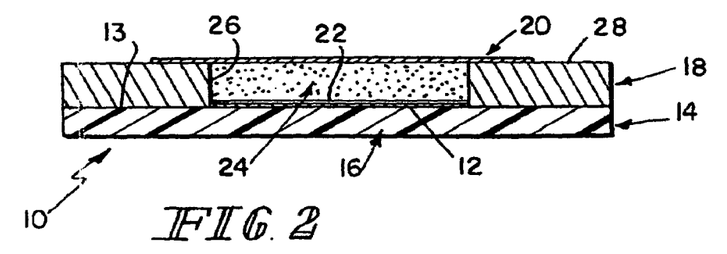
FIG. 2 is a cross-sectional view of the sensor along lines 2-2 of FIG. 1.

A sensor in accordance with the present invention is formed similarly to sensor 10 of FIGS. 1-2, except that it does not include membrane 20. The enzyme and electron mediator is entrapped in a polymer matrix on the electrode. This polymer matrix was prepared by electropolymerization of pyrrole and pyrrole-mediator derivatives. This method entrapped the enzyme in a polymer matrix on the electrode, and, by incorporating mediator-derivatized pyrrole into the polymer, provided for an immobilized mediator for transfer of electrons within the sensor.

Platinum disc electrodes were suitable for preparing sensors in accordance with this method. A mediator which was suitable for copolymerization in a matrix was be prepared by the following reaction sequence:

Synthesis of Pyrrole-Modified Osmium (Bisbipyridyl) Pyridinium Chloride

Pyrrole-modified Osmium (bisbipyridyl) pyridinium Chloride was prepared by the following reaction sequence:

Cleaning Procedure for Platinum Electrodes

The platinum disc electrodes were polished with $Al_2O_3$-paste of decreasing roughness (3 μm, 1 μm, 0.1 μm) on a polishing cloth and were washed with distilled water. Next, the electrodes were cleaned in an ultrasonic bath first in 10 M NaOH and then in 5 M $H_2SO_4$—ten minutes each.

The electrodes underwent electrochemical cycling in oxygen-free 0.5 M $H_2SO_4$:

1. Scan: −610 to +1000 mV vs. $Hg/HgSO_4$ (100 mV/s, 10 μA)
2. Scan: −810 to +1600 mV vs. $Hg/HgSO_4$ (100 mV/s, 10 μA)
3. Scan: −610 to +1000 mV vs. $Hg/HgSO_4$ (100 mV/s, 10 μA)

The third scan was repeated until the cycle voltagram showed a clean platinum surface and stayed constant.

The last step was the polarization at −210 mV for five minutes.

Platinization

Additionally, 4 ml of an oxygen-free 2 mM $H_2PtCl_6$-solution was prepared under Argo in a degassed electrochemical cell. Three voltammetric cycles from +500 to −400 mV vs. Ag/AgCl with a scan rate of 10 mV/s were applied. Then the electrode was washed under argon with oxygen-free distilled water and stored under argon until use.

Polymerization of Pyrrole/Mediator

A pyrrole film was polymerized to contain active Osmium (bis-bipyridyl) pyridinium Chloride as follows:

Co-polymerization was carried out with a mixture of 2 mM pyrrole, 8 mM (9) and 25 mM Tetramethyl ammonium perchlorate (as electrolyte) in 1:1 mixture of acetonitrile: water. 100 Pulses with potential/time of 0 V for 5 sec/1.5 V 1 sec. were carried out. The polymerization was carried out in the absence of oxygen.

Polymerization of Pyrrole-3-Acetic Acid/GDH

In a solution of 50 mM Pyrrole-3-acetic acid, 0.05 mM PQQ, and 50 mM KCl in 0.1 M HEPES buffer, 5 mg/mL of GDH was dissolved. Following a 30 minute incubation to allow for reconstitution of the apoenzyme, the solution was polymerized with potential pulse profile consisting of 20 pulses of 0 V. for 5 sec/1.2 V for 1 second.

Polymerization of Pyrrole-3-Carboxylic Acid/GDH

In a solution of 50 mM Pyrrole-3-carboxylic acid and 50 mM KCl in 0.1 M Hepes buffer, 5 mg/mL of sGDH was dissolved. The solution was polymerized with potential pulse profile consisting of 20 pulses of 0 V. for 5 sec/1.2 V for 1 second, or alternatively of 0 V. for 5 sec/1.4 V for 1 second, or also of 0 V. for 5 sec/1.6 V for 1 second. Potential impacted the sensor performance considerably, indicating the dependence on polypyrrole film properties.

Polymerization of Pyrrole-3-Acetic Acid/Mediator/GDH

In a solution of 50 mM Pyrrole-3-acetic acid, 10 mM Osmium modified pyrrole derivative 10, 0.05 mM PQQ and 50 mM KCl in 0.1 M HEPES buffer 5 mg/mL of sGDH was dissolved. The solution was polymerized with potential pulse profile consisting of 20 pulses of 0 V. for 5 sec/1.4 V for 1 second.

Polymerization of Pyrrole-3-Carboxylic Acid/Mediator/GDH

In a solution of 50 mM Pyrrole-3-acetic acid, 10 mM Osmium modified pyrrole derivative 10, 0.05 mM PQQ and 50 mM KCl in 0.1 M HEPES buffer 5 mg/mL of sGDH was dissolved. The solution was polymerized with potential pulse profile consisting of 20 pulses of 0 V. for 5 sec/1.4 V for 1 second.

Enzyme electrodes were washed with deionized water. It is appreciated, however, that the enzyme electrodes may be washed with a buffer solution or, if necessary, with 3M KCl solution to remove adsorbed GDH and afterwards stored in 0.1 M phosphate buffer pH 7. If electrodes are stored overnight they are kept at 4° C. otherwise at RT.

Evaluation of Sensor Response to Glucose

Figure 11:
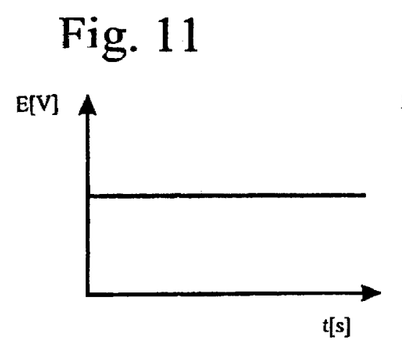
FIG. 11 is a graph showing the measured response for the Pyrrole-3-acetic acid/Mediator/glucose dehydrogenase (GDH) sensor.
Figure 12:
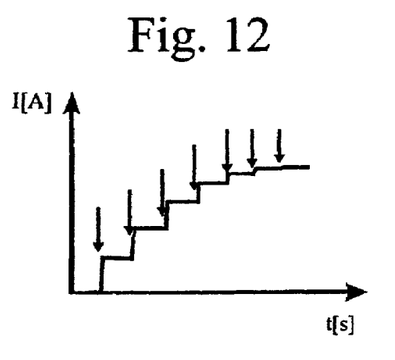
FIG. 12 is a graph showing the measured response for the Pyrrole-3-carboxylic acid/mediator/GDH sensor.

Sensor response was measured by placing the sensor into a stirred PBS (Phosphate buffered saline) buffer along with a reference electrode and a counter electrode. A potential (E) sufficient to oxidize the immobilized mediator was applied, and the solution stirred for a time (t) until the current (I)

stabilized to a low value. See FIG. 11. Aliquots of 1 M glucose solution in PBS were added in a step-wise manner, as shown by arrows in FIG. 12, to the PBS buffer to increase the concentration of glucose in the stirred PBS buffer solution, and the current (I) was measured on the plateau region of the response curve.

Figure 13:
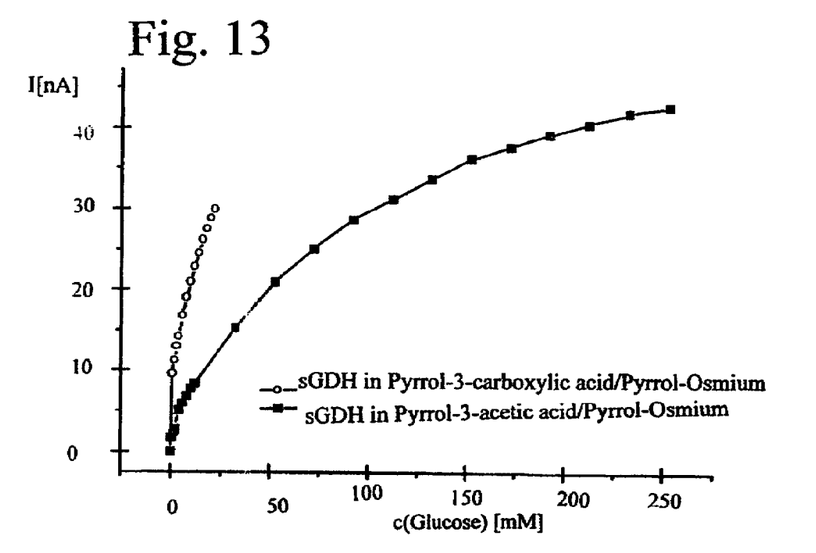
FIG. 13 is a graph showing the response of the Pyrrole-3-acetic acid/Mediator/GDH and the Pyrrole-3-carboxylic acid/mediator/GDH sensors.

Referring now to FIG. 13, the response was measured for the Pyrrole-3-acetic acid/Mediator/GDH and pyrrole-3-carboxylic acid/mediator/GDH sensors. The response shows good electron transfer through the immobilized mediator in the polypyrrole film.

Example 2

Figure 10:
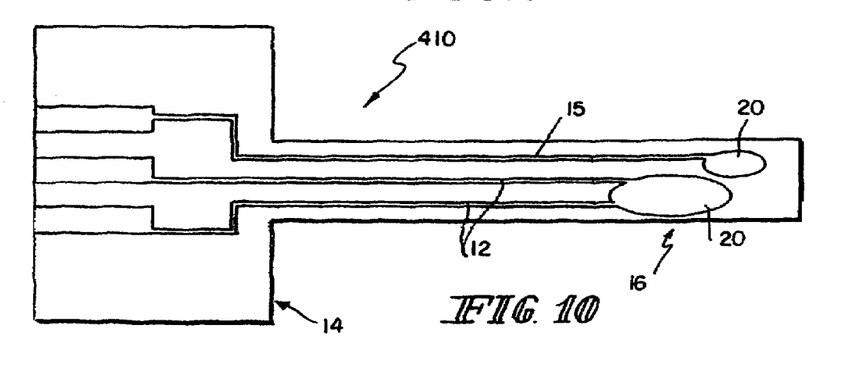
FIG. 10 is similar to FIG. 1 and is a plan view of a sensor in accordance with this invention.

A sensor 410 consists of conductors 12, 15 and reagents deposited on a flat polymeric substrate 14. Materials for encapsulation of the conductors 12, 15 are provided, and reagents that form a semipermeable biocompatible layer over the reagent-containing sensing area 16. See FIG. 10.

Processes and Materials:

Substrate: Polyimid (such as Kapton® polyimide film, which is commercially available from E.I. DuPont de Nemours, Wilmington, Del., and Upilex® polimide film which is commercially available from UBE Industries Ltd, Japan) 0.005" (0.127 mm) thick with gold electrodes and conducting tracks.

Processing: Material is washed with water, acetone, and methylene chloride, then dried at 180° C. for 20 hours. Material is placed in a vacuum chamber and metalized with 50 Å Chromium followed by 500 Å Gold. Metalized material is removed. A laminated photoresist is applied. The resist is exposed, and developed in an aqueous salt solution. Then the metal pattern is developed in a metal etchent solution (typically $HNO_3\_HCl$). The patterned material is rinsed with water, and the remaining photomask is removed with a solvent (typically N-Methylpyrrolidone (NMP). A photodefinable polyimid layer 2 um thick is applied with a spin coater, and solidified by baking at 80° C. for 20 minutes. It is exposed and then developed with a solvent (NMP). It is then baked at 200° C. for 30 minutes to harden the remaining polymer.

Reference/Counter: A silver/silver chloride ink preparation consisting of suspension of silver particles, partially converted to silver chloride on their surfaces, in an organic solvent, i.e. cyclohexanone, with a polymeric suspending agent, such as alginate.

Processing: The ink mixture is applied to the opening in the polyimid and dried for 30 minutes at 80° C. to remove all solvent.

Sensor Area: The opening through the polyimid to the gold electrode is covered with a multilayer reagent area consisting of the following reagents.

Active Enzyme Layer: A solution of Glucose Dehydrogenase/pyrroloquinoline quinone (PQQ) (Enzyme Commission No. 1.1.99.17) and a redox polymer consisting of polyvinylimidazole with bis (bipyridyl) chloro-Osmium in phosphate buffer, optionally with a polyhydric synthetic, natural or semisynthetic polymer, is applied to one electrode opening and dried. A solution of polyethylene glycol diglycidyl ether in aqueous buffer (i.e. 10 mM NaPO4, 150 mM NaCl) is applied to the area, and allowed to react for 10 minutes. The electrodes are then rinsed in physiological saline solution and allowed to dry.

Biocompatibility Layer: The entire structure is placed in a vacuum chamber. A plasma of diglyme is created in the chamber by introducing a low pressure vapor, and applying an RF field to dissociate the diglyme and cause polymerization. After 5 minutes, the diglyme addition is stopped, and the plasma continued for a further 5 minutes. Then the vacuum is broken and the sheet removed from the chamber.

Post-Processing: The sensors 410 are punched from the sheet and mounted into small polycarbonate holders which protect the sensing area and serve as the insertion device. The packaged sensors are sealed into polyethylene bags. The bagged sensors are radiation-sterilized. Ten sterilized sensors are packed into a larger plastic box containing desiccant in the lid. The box is closed and packed into a cardboard outer pack that serves as the final consumer package.

This method for the fabrication of sensors suitable for use according to the current invention utilizes the so-called "wired-enzyme" technology for the immobilization of enzyme and mediator in active relationship within a sensor film. The GDH/PQQ substantially does not react with any endogenous substrate other than the analyte of interest. This allows the sensor to remain inactive, or "off" so long as the electrode is not regenerating the mediator to allow further activity. Sensors produced by this method demonstrate very high sensitivity to glucose and very high current density.

Although the invention has been described in detail with reference to a preferred embodiment, variations and modifications exist within the scope and spirit of the invention as described and defined in the following claims.

What is claimed is:

1. A method for monitoring analyte concentration in a biological fluid by use of a sensor, the method comprising the steps of:

providing a sensor comprising a volume of a hydrophilic medium for retaining an amount of analyte proportionate to the concentration of analyte in a biological fluid in contact with the sensor, an enclosure for said analyte retention volume, an electrode in contact with the hydrophilic medium, a redox enzyme in contact with the medium, and a covalently bound electron transfer mediator that shifts between oxidized and reduced states for facilitating transfer of electrons between the enzyme and the electrode, the enzyme substantially not capable of transferring electrons to or from components of the biological fluid other than said analyte, contacting the biological fluid with the sensor and at initially predetermined intervals intermittently applying a potential to the electrode sufficient to oxidize the electron mediator and sensing current through said electrode during the application of the mediator oxidizing potential, maintaining the applied mediator oxidizing potential at least for a period of time sufficient to determine the rate of change of current with time through the electrode, correlating the current flow resulting from the applied mediator oxidizing potential with the current flow for known concentrations of said analyte in the retention medium, and between the intermittent applications of the mediator oxidizing potential, removing the applied mediator oxidizing potential from the electrode to stop oxidation of the mediator.

2. The method of claim 1 wherein the intervals between the intermittent applied mediator oxidizing potentials are less than the time necessary for the concentration of the analyte in the retention volume to equilibrate with that in the biological fluids in contact with the enclosure.

3. The method of claim 1 further comprising the step of applying a reducing potential to the electrode sufficient to reduce the oxidized form of the electron mediator.

4. The method of claim 1, further comprising retaining the redox enzyme and the mediator in the analyte retention volume by covalently bonding the redox enzyme to a polymer component of a hydrophilic medium.

5. The method of claim 1, further comprising retaining the redox enzyme and the mediator in the analyte retention volume by forming a diffusion-limiting analyte permeable membrane over the electrode.

6. The method of claim 1, wherein the predetermined intervals of intermittently applying a potential to the electrode sufficient to oxidize the electron mediator are of varying duration.

7. A method for monitoring analyte concentration in a biological fluid by use of a sensor, the method comprising the steps of:
   providing a sensor comprising a volume of a hydrophilic medium for retaining an amount of analyte proportionate to the concentration of analyte in a biological fluid in contact with the sensor, an enclosure for said analyte retention volume, an electrode in contact with the hydrophilic medium, a redox enzyme in contact with the medium, and an electron transfer mediator for facilitating transfer of electrons between the enzyme and the electrode, the enzyme substantially not capable of transferring electrons to or from components of the biological fluid other than said analyte,
   contacting the biological fluid with the sensor and at initially predetermined intervals intermittently applying a potential to the electrode sufficient to oxidize the electron mediator and sensing current through said electrode as a function of the duration of the applied potential,
   maintaining the applied mediator oxidizing applied potential at least for a period of time sufficient to determine the rate of change of current with time through the electrode, and
   correlating the current flow with the current flow for known concentrations of said analyte in the retention medium,
   wherein the sensor additionally comprises at least a reference electrode and an auxiliary electrode and the method further comprises the steps of:
   intermittently establishing predetermined level of current to flow between said working electrode and said auxiliary electrode at initially predetermined intervals, and measuring the potential difference between said working electrode and the reference electrode to establish said level of current flow,
   maintaining said level of current flow at least for a period of time sufficient to determine the rate of change of potential necessary to maintain said current through said electrode with time, and
   correlating said potential with the potential for known concentrations of said analyte in the biological fluid.

8. The method of claim 7 wherein the intervals between the intermittent potential measurements are less than the time necessary for the concentration of the analyte in the retention volume to equilibrate with that in the biological fluids in contact with the enclosure.

9. The method of claim 8 wherein the intervals are increased incrementally and the concentration of the analyte in the biological fluid is determined as a function of the rate of increase in analyte concentration in the retention volume.

10. A method for monitoring analyte concentration in a biological fluid by use of a sensor, the method comprising the steps of:
    providing a sensor comprising a volume of a hydrophilic medium for retaining an amount of analyte proportionate to the concentration of analyte in a biological fluid in contact with the sensor, an enclosure for said analyte retention volume, an electrode in contact with the hydrophilic medium, a redox enzyme in contact with the medium, and an electron transfer mediator for facilitating transfer of electrons between the enzyme and the electrode, the enzyme substantially not capable of transferring electrons to or from components of the biological fluid other than said analyte,
    contacting the biological fluid with the sensor and at initially predetermined intervals intermittently applying a potential to the electrode sufficient to oxidize the electron mediator and sensing current through said electrode as a function of the duration of the applied potential,
    retaining the redox enzyme and the mediator in the analyte retention volume by covalently bonding the mediator and the redox enzyme to the enclosure,
    maintaining the applied mediator oxidizing potential at least for a period of time sufficient to determine the rate of change of current with time through the electrode, and
    correlating the current flow with the current flow for known concentrations of said analyte in the retention medium.

11. A method for monitoring analyte concentration in a biological fluid, comprising:
    providing a sensor comprising a volume of a hydrophilic medium for retaining an amount of analyte in a biological fluid, an enclosure for said analyte retention volume, an electrode in contact with the hydrophilic medium, a redox enzyme in contact with the medium, and an electron transfer mediator for facilitating transfer of electrons between the enzyme and the electrode, the enzyme substantially not capable of transferring electrons to or from components of the biological fluid other than said analyte;
    contacting the biological fluid with the sensor and allowing an analyte of the biological fluid to diffuse into the analyte retention volume;
    varying the potential of the electrode over time from a mediator oxidizing potential sufficient to oxidize the electron mediator, to a potential at which no oxidation of the mediator occurs, to a reduction potential at which reduction of the mediator takes place;
    maintaining the mediator oxidizing applied potential at least for a period of time sufficient to determine the rate of change of current with time through the electrode; and
    sensing current through said electrode during application of the mediator oxidizing potential and correlating the sensed current with concentration of said analyte in the retention volume.

12. The method of claim 11, wherein at least one of the mediator oxidizing potential and the reduction potential is applied in pulses of varying pulse width.

13. The method of claim 11, wherein at least one of the mediator oxidizing potential and the reduction potential is applied in pulses and the intervals between pulses have varying durations.

14. A method for monitoring analyte concentration in a biological fluid, comprising:
    providing a sensor comprising a volume of a hydrophilic medium for retaining an amount of analyte in a biological fluid, an enclosure for said analyte retention volume, an electrode in contact with the hydrophilic medium, a redox enzyme in contact with the medium, and a covalently bound electron transfer mediator that shifts between oxidized and reduced states for facilitating transfer of electrons between the enzyme and the electrode, the enzyme substantially not capable of transferring electrons to or from components of the biological fluid other than said analyte;

contacting the biological fluid with the sensor and allowing an analyte of the biological fluid to diffuse into the analyte retention volume;

applying in pulses of varying width a mediator oxidizing potential sufficient to oxidize the electron mediator to a potential at which no oxidation of the mediator occurs;

maintaining the duration of the pulses of applied mediator oxidizing potential for a period of time sufficient to determine the rate of change of current with time through the electrode; and sensing current through said electrode during application of the mediator oxidizing potential and correlating the sensed current with concentration of said analyte in the retention volume.

15. The method of claim 14, further comprising applying a reduction potential to the electrode sufficient to reduce the oxidized form of the electron mediator.

16. The method of claim 14, further comprising varying the duration of the intervals between the pulses of mediator oxidizing potential.

17. A method for monitoring analyte concentration in a biological fluid, comprising:

providing a sensor comprising a volume of a hydrophilic medium for retaining an amount of analyte in a biological fluid, an enclosure for said analyte retention volume, an electrode in contact with the hydrophilic medium, a redox enzyme in contact with the medium, and a covalently bound electron transfer mediator that shifts between oxidized and reduced states for facilitating transfer of electrons between the enzyme and the electrode;

contacting the biological fluid with the sensor and allowing an analyte of the biological fluid to diffuse into the analyte retention volume;

intermittently varying the potential of the electrode over time from a first potential at which no oxidation of the mediator takes place, to a second potential at which oxidation of the electron mediator takes place, to a third potential at which no oxidation of the mediator takes place;

maintaining the second potential at least for a period of time sufficient to determine the rate of change of current with time through the electrode; and sensing current through said electrode during application of the second potential and correlating the sensed current with concentration of said analyte in the retention volume.

18. The method of claim 17, wherein the first and third potentials are different.

19. The method claim 17, wherein at least one of the first, second and third potentials is applied in pulses of varying pulse width.

20. The method of claim 17, wherein at least one of the first, second and third potentials is applied in pulses and the intervals between pulses have varying durations.

21. The method of claim 17, wherein one of the first and third potentials is zero.

22. The method of claim 17, wherein the first and third potentials are the same.

23. The method claim 17, wherein one of the first and third potentials is sufficient to reduce the oxidized form of the electron mediator.

24. The method of claim 17, further comprising retaining the redox enzyme and the mediator in the analyte retention volume by entrapping the redox enzyme and mediator in a hydrophilic matrix on the electrode.

25. The method of claim 17, further comprising retaining the redox enzyme and mediator in the analyte retention volume.

26. The method of claim 25, further comprising covalently bonding the redox enzyme to a polymer component of a hydrophilic medium.

27. The method of claim 17, further comprising retaining the redox enzyme and the mediator in the analyte retention volume by forming a diffusion-limiting analyte permeable membrane over the electrode.

* * * * *

UNITED STATES PATENT AND TRADEMARK OFFICE
CERTIFICATE OF CORRECTION

| | | |
|---|---|---|
| PATENT NO. | : 7,731,835 B2 | Page 1 of 1 |
| APPLICATION NO. | : 11/038970 | |
| DATED | : June 8, 2010 | |
| INVENTOR(S) | : Buck et al. | |

It is certified that error appears in the above-identified patent and that said Letters Patent is hereby corrected as shown below:

Col. 19, Claim 17, lines 30 and 31:

Replace "a covalently bound" with --an exogeneous--

Signed and Sealed this

Tenth Day of August, 2010

David J. Kappos
*Director of the United States Patent and Trademark Office*